United States Patent
Ishikawa et al.

(10) Patent No.: US 6,841,374 B1
(45) Date of Patent: Jan. 11, 2005

(54) ENHANCED IMMUNOGEN FOR INACTIVATED VACCINE FOR INFECTION WITH JAPANESE ENCEPHALITIS VIRUSES AND PROCESS FOR PRODUCING THE SAME

(75) Inventors: Toyokazu Ishikawa, Kagawa-ken (JP);
Hironori Yoshii, Kagawa-ken (JP);
Toshiyuki Onishi, Kagawa-ken (JP);
Tadashi Imagawa, Kagawa-ken (JP);
Masahide Ishibashi, Kagawa-ken (JP)

(73) Assignee: Research Foundation for Microbial Diseases of Osaka University, Osaka (JP)

( * ) Notice: Subject to any disclaimer, the term of this patent is extended or adjusted under 35 U.S.C. 154(b) by 0 days.

(21) Appl. No.: 09/555,704
(22) PCT Filed: Jun. 2, 1999
(86) PCT No.: PCT/JP99/02931

§ 371 (c)(1),
(2), (4) Date: Nov. 7, 2000

(87) PCT Pub. No.: WO00/20565

PCT Pub. Date: Apr. 13, 2000

(30) Foreign Application Priority Data

Oct. 5, 1998 (JP) ............................................ 10-319762

(51) Int. Cl.[7] ............................ C12N 7/02; A61K 39/12
(52) U.S. Cl. .................... 435/239; 435/235.1; 435/236; 424/204.1; 424/218.1
(58) Field of Search .......................... 424/184.1, 204.1, 424/218.1, 159.1; 435/235.1, 236, 237, 238, 239

(56) References Cited

U.S. PATENT DOCUMENTS

| | | | |
|---|---|---|---|
| 4,725,546 A | 2/1988 | Sakamoto et al. | |
| 5,719,051 A | 2/1998 | Mundt et al. | 435/235.1 |
| 6,207,439 B1 * | 3/2001 | Liau et al. | 435/239 |

FOREIGN PATENT DOCUMENTS

| | | |
|---|---|---|
| CA | 2286690 | 10/1998 |
| CA | 2301000 | 3/1999 |
| JP | 61-53227 | 3/1986 |
| JP | 7-265093 | 10/1995 |
| WO | WO 91/09935 | 7/1991 |
| WO | WO 97/04803 A1 | 2/1997 |
| WO | WO 99/11762 | 3/1999 |

OTHER PUBLICATIONS

Huiying, S., et al., "The Study on Adaptation of Japanese Encephalitis Virus in Vero Cells" Virologica Sinica 10(4):277 (1995) abstract only.

Huiying, S., et al., "Large–Scale Purification of Inactivated Japanese Encephalitis Vaccine from Vero Cells by Zonal Centrifugation" Virologica Sinica 13(3):213 (1998) abstract only.

Takegami, T., et al., "Inhibitory effect of furanonaphthoquinone derivatives on the replication of Japanese encephalitis virus" Antiviral Research 37:37–45 (1998).

Ding, Z., et al., Zhonghua Yi Za Zhi 78(4):261–262 (1998).

International Search Report from Application No. EP 99 92 3858, (2001).

* cited by examiner

Primary Examiner—James Housel
Assistant Examiner—Stacy B. Chen
(74) Attorney, Agent, or Firm—Jacqueline F. Mahoney; Judy M. Mohr; Perkins Coie LLP

(57) ABSTRACT

The present invention provides a novel inactivated virus particle and a reinforced immunogen which have a reinforced titer about twice to about 10 times that of a conventional vaccine, as well as a method for producing the same. The inactivated virus particle is produced by inactivating and then purifying a culture by physical means. The inactivated virus particle of the present invention is useful in a diagnostic agent for infectious disease caused by a group of Japanese encephalitis virus.

10 Claims, 1 Drawing Sheet

Fig. 1

A

B

SEQUENCE LISTING

```
<160> NUMBER OF SEQ ID NOS: 4

<210> SEQ ID NO 1
<211> LENGTH: 1500
<212> TYPE: DNA
<213> ORGANISM: Japanese encephalitis virus
<220> FEATURE:
<221> NAME/KEY: CDS
<222> LOCATION: (1)..(1500)
```

<400> SEQUENCE: 1

```
ttt aac tgt ctg gga atg ggg aat cgg gat ttc ata gaa gga gcc agt         48
Phe Asn Cys Leu Gly Met Gly Asn Arg Asp Phe Ile Glu Gly Ala Ser
 1               5                  10                  15 gga gcc act tgg gtg gat ttg gtg tta gaa gga gat agt tgt ttg aca         96
Gly Ala Thr Trp Val Asp Leu Val Leu Glu Gly Asp Ser Cys Leu Thr
             20                  25                  30 atc atg gca aac gac aaa cca aca cta gat gtc cgc atg atc aac att        144
Ile Met Ala Asn Asp Lys Pro Thr Leu Asp Val Arg Met Ile Asn Ile
         35                  40                  45 gaa gct agc caa ctt gct gaa gtc agg agt tac tgc tat cac gct tca        192
Glu Ala Ser Gln Leu Ala Glu Val Arg Ser Tyr Cys Tyr His Ala Ser
     50                  55                  60 gtc act gac att tca acg gtg gct cga tgc ccc acg act gga gaa gcc        240
Val Thr Asp Ile Ser Thr Val Ala Arg Cys Pro Thr Thr Gly Glu Ala
 65                  70                  75                  80 cac aac gag aaa cgt gct gac agc agc tac gtg tgc aaa caa ggc ttt        288
His Asn Glu Lys Arg Ala Asp Ser Ser Tyr Val Cys Lys Gln Gly Phe
                 85                  90                  95 act gac cgc gga tgg gga aat gga tgt gga ctt ttc ggg aaa gga agc        336
Thr Asp Arg Gly Trp Gly Asn Gly Cys Gly Leu Phe Gly Lys Gly Ser
            100                 105                 110 att gac aca tgc gca aaa ttt tct tgt acc agt aag gcc att gga aga        384
Ile Asp Thr Cys Ala Lys Phe Ser Cys Thr Ser Lys Ala Ile Gly Arg
        115                 120                 125 atg atc caa cca gag aac atc aag tac gag gtt ggc ata ttc gtg cac        432
Met Ile Gln Pro Glu Asn Ile Lys Tyr Glu Val Gly Ile Phe Val His
130                 135                 140 ggg acc acc acc tcg gaa aac cat ggg aat tac tca gcg caa gta gga        480
Gly Thr Thr Thr Ser Glu Asn His Gly Asn Tyr Ser Ala Gln Val Gly
145                 150                 155                 160 gcg tct caa gca gca aag ttt act gta act cca aac gct ccc tca ata        528
Ala Ser Gln Ala Ala Lys Phe Thr Val Thr Pro Asn Ala Pro Ser Ile
                165                 170                 175 acc ctc aag ctt ggt gat tat gga gag gtc aca ctg gat tgt gaa cca        576
Thr Leu Lys Leu Gly Asp Tyr Gly Glu Val Thr Leu Asp Cys Glu Pro
            180                 185                 190 agg agt gga ctg aac act gaa gcg ttc tat gtc atg acc gtg ggt tcg        624
Arg Ser Gly Leu Asn Thr Glu Ala Phe Tyr Val Met Thr Val Gly Ser
        195                 200                 205 aag tca ttc tta gtc cat agg gaa tgg ttc cat gac ctt tct ctt ccc        672
Lys Ser Phe Leu Val His Arg Glu Trp Phe His Asp Leu Ser Leu Pro
    210                 215                 220 tgg acg tcc cct tca agc acg gca tgg agg aac aga gaa ctc ctc atg        720
Trp Thr Ser Pro Ser Ser Thr Ala Trp Arg Asn Arg Glu Leu Leu Met
225                 230                 235                 240 gaa ttt gaa gag gca cat gcc aca aaa caa tct gtc gta gcc ctt ggg        768
Glu Phe Glu Glu Ala His Ala Thr Lys Gln Ser Val Val Ala Leu Gly
                245                 250                 255 tca cag gag gga ggc ctc cat caa gcg ttg gca gga gcc atc gtg gtg        816
Ser Gln Glu Gly Gly Leu His Gln Ala Leu Ala Gly Ala Ile Val Val
            260                 265                 270 gag tac tcg agc tca gtg aag tta aca tca ggt cac ctg aaa tgc agg        864
Glu Tyr Ser Ser Ser Val Lys Leu Thr Ser Gly His Leu Lys Cys Arg
        275                 280                 285 cta aaa atg gac aaa ctg gct ctg aag ggc acg act tat ggc atg tgt        912
Leu Lys Met Asp Lys Leu Ala Leu Lys Gly Thr Thr Tyr Gly Met Cys
    290                 295                 300 aca gaa aaa ttc tcg ttc gcg aaa aat cca gcg gac aca ggc cat gga        960
```

```

Thr Glu Lys Phe Ser Phe Ala Lys Asn Pro Ala Asp Thr Gly His Gly
305                 310                 315                 320 aca gtt gtc att gag ctc aca tat tct gga agc gat ggc tcc tgt aaa        1008
Thr Val Val Ile Glu Leu Thr Tyr Ser Gly Ser Asp Gly Ser Cys Lys
                325                 330                 335 att ccg att gtc tca gtt gcg agc ctc aat gac atg acc cct gtg ggg        1056
Ile Pro Ile Val Ser Val Ala Ser Leu Asn Asp Met Thr Pro Val Gly
            340                 345                 350 agg ctg gta aca gta aac ccc ttc gtt gcg aca tct agc tcc aac tca        1104
Arg Leu Val Thr Val Asn Pro Phe Val Ala Thr Ser Ser Ser Asn Ser
        355                 360                 365 aag gtg ctg gtt gag atg gaa cct ccc ttc gga gac tct tat atc gtg        1152
Lys Val Leu Val Glu Met Glu Pro Pro Phe Gly Asp Ser Tyr Ile Val
    370                 375                 380 gtt gga aga ggg gac aag cag att aac cat cac tgg cac aaa gct gga        1200
Val Gly Arg Gly Asp Lys Gln Ile Asn His His Trp His Lys Ala Gly
385                 390                 395                 400 agc acg ctg ggc aaa gcc ttc tca aca act ttg aaa ggg gct cag aga        1248
Ser Thr Leu Gly Lys Ala Phe Ser Thr Thr Leu Lys Gly Ala Gln Arg
                405                 410                 415 tta gca gcg cta ggt gac aca gcc tgg gac ttc ggc tcc att gga ggg        1296
Leu Ala Ala Leu Gly Asp Thr Ala Trp Asp Phe Gly Ser Ile Gly Gly
            420                 425                 430 gta ttc aac tcc ata ggg aaa gct gtt cac caa gta ttt ggc ggt gca        1344
Val Phe Asn Ser Ile Gly Lys Ala Val His Gln Val Phe Gly Gly Ala
        435                 440                 445 ttc aga acg ctc ttt ggg gga atg tct tgg atc aca caa gga cta atg        1392
Phe Arg Thr Leu Phe Gly Gly Met Ser Trp Ile Thr Gln Gly Leu Met
    450                 455                 460 ggg gcc ttg ctt ctt tgg atg ggt gtc aac gca cga gac cgg tca atc        1440
Gly Ala Leu Leu Leu Trp Met Gly Val Asn Ala Arg Asp Arg Ser Ile
465                 470                 475                 480 gcc ctg gct ttt ttg gcc acg gga ggt gtg ctc gtg ttt tta gcg acc        1488
Ala Leu Ala Phe Leu Ala Thr Gly Gly Val Leu Val Phe Leu Ala Thr
                485                 490                 495 aat gtg cat gcc                                                        1500
Asn Val His Ala
        500

<210> SEQ ID NO 2
<211> LENGTH: 500
<212> TYPE: PRT
<213> ORGANISM: Japanese encephalitis virus

<400> SEQUENCE: 2

Phe Asn Cys Leu Gly Met Gly Asn Arg Asp Phe Ile Glu Gly Ala Ser
1               5                   10                  15

Gly Ala Thr Trp Val Asp Leu Val Leu Glu Gly Asp Ser Cys Leu Thr
                20                  25                  30

Ile Met Ala Asn Asp Lys Pro Thr Leu Asp Val Arg Met Ile Asn Ile
            35                  40                  45

Glu Ala Ser Gln Leu Ala Glu Val Arg Ser Tyr Cys Tyr His Ala Ser
        50                  55                  60

Val Thr Asp Ile Ser Thr Val Ala Arg Cys Pro Thr Thr Gly Glu Ala
65                  70                  75                  80

His Asn Glu Lys Arg Ala Asp Ser Ser Tyr Val Cys Lys Gln Gly Phe
                85                  90                  95

Thr Asp Arg Gly Trp Gly Asn Gly Cys Gly Leu Phe Gly Lys Gly Ser
            100                 105                 110
```

-continued

```
Ile Asp Thr Cys Ala Lys Phe Ser Cys Thr Ser Lys Ala Ile Gly Arg
        115                 120                 125

Met Ile Gln Pro Glu Asn Ile Lys Tyr Glu Val Gly Ile Phe Val His
    130                 135                 140

Gly Thr Thr Thr Ser Glu Asn His Gly Asn Tyr Ser Ala Gln Val Gly
145                 150                 155                 160

Ala Ser Gln Ala Ala Lys Phe Thr Val Thr Pro Asn Ala Pro Ser Ile
                165                 170                 175

Thr Leu Lys Leu Gly Asp Tyr Gly Glu Val Thr Leu Asp Cys Glu Pro
            180                 185                 190

Arg Ser Gly Leu Asn Thr Glu Ala Phe Tyr Val Met Thr Val Gly Ser
        195                 200                 205

Lys Ser Phe Leu Val His Arg Glu Trp Phe His Asp Leu Ser Leu Pro
    210                 215                 220

Trp Thr Ser Pro Ser Ser Thr Ala Trp Arg Asn Arg Glu Leu Leu Met
225                 230                 235                 240

Glu Phe Glu Glu Ala His Ala Thr Lys Gln Ser Val Val Ala Leu Gly
                245                 250                 255

Ser Gln Glu Gly Gly Leu His Gln Ala Leu Ala Gly Ala Ile Val Val
            260                 265                 270

Glu Tyr Ser Ser Ser Val Lys Leu Thr Ser Gly His Leu Lys Cys Arg
        275                 280                 285

Leu Lys Met Asp Lys Leu Ala Leu Lys Gly Thr Thr Tyr Gly Met Cys
    290                 295                 300

Thr Glu Lys Phe Ser Phe Ala Lys Asn Pro Ala Asp Thr Gly His Gly
305                 310                 315                 320

Thr Val Val Ile Glu Leu Thr Tyr Ser Gly Ser Asp Gly Ser Cys Lys
                325                 330                 335

Ile Pro Ile Val Ser Val Ala Ser Leu Asn Asp Met Thr Pro Val Gly
            340                 345                 350

Arg Leu Val Thr Val Asn Pro Phe Val Ala Thr Ser Ser Ser Asn Ser
        355                 360                 365

Lys Val Leu Val Glu Met Glu Pro Pro Phe Gly Asp Ser Tyr Ile Val
    370                 375                 380

Val Gly Arg Gly Asp Lys Gln Ile Asn His His Trp His Lys Ala Gly
385                 390                 395                 400

Ser Thr Leu Gly Lys Ala Phe Ser Thr Thr Leu Lys Gly Ala Gln Arg
                405                 410                 415

Leu Ala Ala Leu Gly Asp Thr Ala Trp Asp Phe Gly Ser Ile Gly Gly
            420                 425                 430

Val Phe Asn Ser Ile Gly Lys Ala Val His Gln Val Phe Gly Gly Ala
        435                 440                 445

Phe Arg Thr Leu Phe Gly Gly Met Ser Trp Ile Thr Gln Gly Leu Met
    450                 455                 460

Gly Ala Leu Leu Leu Trp Met Gly Val Asn Ala Arg Asp Arg Ser Ile
465                 470                 475                 480

Ala Leu Ala Phe Leu Ala Thr Gly Gly Val Leu Val Phe Leu Ala Thr
                485                 490                 495

Asn Val His Ala
            500
```

<210> SEQ ID NO 3
<211> LENGTH: 1500

<212> TYPE: DNA
<213> ORGANISM: Japanese encephalitis virus
<220> FEATURE:
<221> NAME/KEY: CDS
<222> LOCATION: (1)..(1500)

<400> SEQUENCE: 3

```
ttc aac tgt ctg gga atg ggc aat cgt gac ttc ata gaa gga gcc agt      48
Phe Asn Cys Leu Gly Met Gly Asn Arg Asp Phe Ile Glu Gly Ala Ser
1               5                   10                  15 gga gcc act tgg gtg gac ttg gtg cta gaa gga gac agc tgc ttg aca      96
Gly Ala Thr Trp Val Asp Leu Val Leu Glu Gly Asp Ser Cys Leu Thr
            20                  25                  30 atc atg gca aac gac aaa cca aca ttg gac gtc cgc atg atc aac atc     144
Ile Met Ala Asn Asp Lys Pro Thr Leu Asp Val Arg Met Ile Asn Ile
        35                  40                  45 gaa gct agc caa ctt gct gag gtc aga agt tac tgc tat cat gct tca     192
Glu Ala Ser Gln Leu Ala Glu Val Arg Ser Tyr Cys Tyr His Ala Ser
    50                  55                  60 gtc act gac atc tcg acg gtg gct cgg tgc ccc acg act gga gaa gcc     240
Val Thr Asp Ile Ser Thr Val Ala Arg Cys Pro Thr Thr Gly Glu Ala
65                  70                  75                  80 cac aac gag aag cga gct gat agt agc tat gtg tgc aaa caa ggc ttc     288
His Asn Glu Lys Arg Ala Asp Ser Ser Tyr Val Cys Lys Gln Gly Phe
                85                  90                  95 act gat cgt ggg tgg ggc aac gga tgt gga ctt ttc ggg aag gga agt     336
Thr Asp Arg Gly Trp Gly Asn Gly Cys Gly Leu Phe Gly Lys Gly Ser
            100                 105                 110 att gac aca tgt gca aaa ttc tcc tgc acc agg aaa gcg att ggg aga     384
Ile Asp Thr Cys Ala Lys Phe Ser Cys Thr Arg Lys Ala Ile Gly Arg
        115                 120                 125 aca atc cag cca gaa aac atc aaa tac gaa gtt ggc att ttt gtg cat     432
Thr Ile Gln Pro Glu Asn Ile Lys Tyr Glu Val Gly Ile Phe Val His
    130                 135                 140 gga acc acc act tcg gaa aac cat ggg aat tat tca gcg caa gtt ggg     480
Gly Thr Thr Thr Ser Glu Asn His Gly Asn Tyr Ser Ala Gln Val Gly
145                 150                 155                 160 gcg tcc cag gcg gca aag ttt aca gta aca cct aat gct cct tcg ata     528
Ala Ser Gln Ala Ala Lys Phe Thr Val Thr Pro Asn Ala Pro Ser Ile
                165                 170                 175 acc ctc aaa ctt ggt gac tac gga gaa gtc aca ctg gac tgt gag cca     576
Thr Leu Lys Leu Gly Asp Tyr Gly Glu Val Thr Leu Asp Cys Glu Pro
            180                 185                 190 agg agt gga cta aac act gaa gcg ttt tac gtc atg acc gtg ggg tca     624
Arg Ser Gly Leu Asn Thr Glu Ala Phe Tyr Val Met Thr Val Gly Ser
        195                 200                 205 aag tca ttt ttg gtc cat agg gaa tgg ttt cat gac ctc gct ctc cct     672
Lys Ser Phe Leu Val His Arg Glu Trp Phe His Asp Leu Ala Leu Pro
    210                 215                 220 tgg acg ccc cct tcg agc aca gcg tgg aga aac aga gaa ctc ctc atg     720
Trp Thr Pro Pro Ser Ser Thr Ala Trp Arg Asn Arg Glu Leu Leu Met
225                 230                 235                 240 gaa ttt gaa gag gcg cac gcc aca aaa cag tcc gtt gtt gct ctt ggg     768
Glu Phe Glu Glu Ala His Ala Thr Lys Gln Ser Val Val Ala Leu Gly
                245                 250                 255 tca cag gaa gga ggc ctc cat cag gcg ttg gca gga gcc atc gtg gtg     816
Ser Gln Glu Gly Gly Leu His Gln Ala Leu Ala Gly Ala Ile Val Val
            260                 265                 270 gag tac tca agc tca gtg aag tta aca tca ggc cac cta aaa tgc agg     864
Glu Tyr Ser Ser Ser Val Lys Leu Thr Ser Gly His Leu Lys Cys Arg
        275                 280                 285
```

```
ctg aaa atg gac aaa ctg gct ctg aaa ggc aca acc tat ggt atg tgc      912
Leu Lys Met Asp Lys Leu Ala Leu Lys Gly Thr Thr Tyr Gly Met Cys
    290                 295                 300 aca gaa aaa ttc tcg ttc gcg aaa aat ccg gcg gac act ggt cac gga      960
Thr Glu Lys Phe Ser Phe Ala Lys Asn Pro Ala Asp Thr Gly His Gly
305                 310                 315                 320 aca gtt gtc att gaa ctt tca tac tct ggg agt gat ggc ccc tgc aag     1008
Thr Val Val Ile Glu Leu Ser Tyr Ser Gly Ser Asp Gly Pro Cys Lys
                325                 330                 335 att ccg att gtc tcc gtt gct agc ctc aat gac atg acc ccc gtc ggg     1056
Ile Pro Ile Val Ser Val Ala Ser Leu Asn Asp Met Thr Pro Val Gly
            340                 345                 350 cgg ctg gtg aca gtg aac ccc ttc gtc gcg act tcc agc gcc aac tca     1104
Arg Leu Val Thr Val Asn Pro Phe Val Ala Thr Ser Ser Ala Asn Ser
        355                 360                 365 aag gtg ctg gtc gag atg gaa ccc ccc ttc gga gac tcc tac atc gta     1152
Lys Val Leu Val Glu Met Glu Pro Pro Phe Gly Asp Ser Tyr Ile Val
370                 375                 380 gtt gga agg gga gac aag cag att aac cac cat tgg tac aag gct gga     1200
Val Gly Arg Gly Asp Lys Gln Ile Asn His His Trp Tyr Lys Ala Gly
385                 390                 395                 400 agc acg ctg ggc aaa gcc ttt tca acg act ttg aag gga gct caa aga     1248
Ser Thr Leu Gly Lys Ala Phe Ser Thr Thr Leu Lys Gly Ala Gln Arg
                405                 410                 415 ctg gca gcg ttg ggc gac aca gcc tgg gac ttt ggc tct att gga ggg     1296
Leu Ala Ala Leu Gly Asp Thr Ala Trp Asp Phe Gly Ser Ile Gly Gly
            420                 425                 430 gtc ttc aac tcc ata ggg aaa gct gtt cac caa gtg ttt ggt ggt gcc     1344
Val Phe Asn Ser Ile Gly Lys Ala Val His Gln Val Phe Gly Gly Ala
        435                 440                 445 ttc aga aca ctc ttt ggg gga atg tct tgg atc aca caa ggg cta atg     1392
Phe Arg Thr Leu Phe Gly Gly Met Ser Trp Ile Thr Gln Gly Leu Met
450                 455                 460 ggg gcc cta cta ctt tgg atg ggc atc aac gca cga gac cga tca att     1440
Gly Ala Leu Leu Leu Trp Met Gly Ile Asn Ala Arg Asp Arg Ser Ile
465                 470                 475                 480 gct ttg gcc ttc tta gcc aca gga ggt gtg ctc gtg ttc tta gct acc     1488
Ala Leu Ala Phe Leu Ala Thr Gly Gly Val Leu Val Phe Leu Ala Thr
                485                 490                 495 aat gtg cat gct                                                     1500
Asn Val His Ala
            500

<210> SEQ ID NO 4
<211> LENGTH: 500
<212> TYPE: PRT
<213> ORGANISM: Japanese encephalitis virus

<400> SEQUENCE: 4

Phe Asn Cys Leu Gly Met Gly Asn Arg Asp Phe Ile Glu Gly Ala Ser
 1               5                  10                  15

Gly Ala Thr Trp Val Asp Leu Val Leu Glu Gly Asp Ser Cys Leu Thr
            20                  25                  30

Ile Met Ala Asn Asp Lys Pro Thr Leu Asp Val Arg Met Ile Asn Ile
        35                  40                  45

Glu Ala Ser Gln Leu Ala Glu Val Arg Ser Tyr Cys Tyr His Ala Ser
    50                  55                  60

Val Thr Asp Ile Ser Thr Val Ala Arg Cys Pro Thr Thr Gly Glu Ala
65                  70                  75                  80
```

```
His Asn Glu Lys Arg Ala Asp Ser Ser Tyr Val Cys Lys Gln Gly Phe
                85                  90                  95
Thr Asp Arg Gly Trp Gly Asn Gly Cys Gly Leu Phe Gly Lys Gly Ser
            100                 105                 110
Ile Asp Thr Cys Ala Lys Phe Ser Cys Thr Arg Lys Ala Ile Gly Arg
        115                 120                 125
Thr Ile Gln Pro Glu Asn Ile Lys Tyr Glu Val Gly Ile Phe Val His
    130                 135                 140
Gly Thr Thr Thr Ser Glu Asn His Gly Asn Tyr Ser Ala Gln Val Gly
145                 150                 155                 160
Ala Ser Gln Ala Ala Lys Phe Thr Val Thr Pro Asn Ala Pro Ser Ile
                165                 170                 175
Thr Leu Lys Leu Gly Asp Tyr Gly Glu Val Thr Leu Asp Cys Glu Pro
            180                 185                 190
Arg Ser Gly Leu Asn Thr Glu Ala Phe Tyr Val Met Thr Val Gly Ser
        195                 200                 205
Lys Ser Phe Leu Val His Arg Glu Trp Phe His Asp Leu Ala Leu Pro
    210                 215                 220
Trp Thr Pro Pro Ser Ser Thr Ala Trp Arg Asn Arg Glu Leu Leu Met
225                 230                 235                 240
Glu Phe Glu Glu Ala His Ala Thr Lys Gln Ser Val Val Ala Leu Gly
                245                 250                 255
Ser Gln Glu Gly Gly Leu His Gln Ala Leu Ala Gly Ala Ile Val Val
            260                 265                 270
Glu Tyr Ser Ser Ser Val Lys Leu Thr Ser Gly His Leu Lys Cys Arg
        275                 280                 285
Leu Lys Met Asp Lys Leu Ala Leu Lys Gly Thr Thr Tyr Gly Met Cys
    290                 295                 300
Thr Glu Lys Phe Ser Phe Ala Lys Asn Pro Ala Asp Thr Gly His Gly
305                 310                 315                 320
Thr Val Val Ile Glu Leu Ser Tyr Ser Gly Ser Asp Gly Pro Cys Lys
                325                 330                 335
Ile Pro Ile Val Ser Val Ala Ser Leu Asn Asp Met Thr Pro Val Gly
            340                 345                 350
Arg Leu Val Thr Val Asn Pro Phe Val Ala Thr Ser Ser Ala Asn Ser
        355                 360                 365
Lys Val Leu Val Glu Met Glu Pro Pro Phe Gly Asp Ser Tyr Ile Val
    370                 375                 380
Val Gly Arg Gly Asp Lys Gln Ile Asn His His Trp Tyr Lys Ala Gly
385                 390                 395                 400
Ser Thr Leu Gly Lys Ala Phe Ser Thr Thr Leu Lys Gly Ala Gln Arg
                405                 410                 415
Leu Ala Ala Leu Gly Asp Thr Ala Trp Asp Phe Gly Ser Ile Gly Gly
            420                 425                 430
Val Phe Asn Ser Ile Gly Lys Ala Val His Gln Val Phe Gly Gly Ala
        435                 440                 445
Phe Arg Thr Leu Phe Gly Gly Met Ser Trp Ile Thr Gln Gly Leu Met
    450                 455                 460
Gly Ala Leu Leu Leu Trp Met Gly Ile Asn Ala Arg Asp Arg Ser Ile
465                 470                 475                 480
```

```
-continued

Ala Leu Ala Phe Leu Ala Thr Gly Gly Val Leu Val Phe Leu Ala Thr
            485                 490                 495
Asn Val His Ala
        500
```

ENHANCED IMMUNOGEN FOR INACTIVATED VACCINE FOR INFECTION WITH JAPANESE ENCEPHALITIS VIRUSES AND PROCESS FOR PRODUCING THE SAME

This application claims priority to application no. PCT/JP99/02931 filed Jun. 2, 1999, now publication no. WO 00/20565 published Apr. 13, 2000; which claims priority to JP 10-319762 filed Oct. 5, 1998, which are both incorporated herein by reference.

BACKGROUND OF THE INVENTION

1. Field of the Invention

The present invention relates to an inactivated vaccine against infectious disease caused by a group of Japanese encephalitis viruses of *Flavivirus*, and a diagnostic agent thereof. In particular, the present invention relates to an inactivated vaccine against Japanese encephalitis, a reinforced immunogen or antigen which is outstanding and useful as an active ingredient of the vaccine, and a method for producing the immunogen or antigen.

2. Description of the Related Art

Hereinafter, as a representative example of infectious disease caused by a group of Japanese encephalitis viruses, Japanese encephalitis will be illustrated, and a vaccine against it will be described. The first Japanese encephalitis vaccine was put into practical use in 1954. This vaccine contains, as its active ingredient, an antigen prepared from virus cultured in mouse brain. The purity of such a vaccine is low, and such a vaccine contains a lot of contamination, so that it might induce an allergic neurological disorder in the central nervous system. Thereafter, an improved high-purity vaccine obtained by the combination of alcohol sedimentation, treatment with protamine sulfate, ultracentrifugation, and the like was put into practical use in 1965. Thus, the quality of the vaccine was remarkably improved. Such a vaccine and a production technique therefor have been utilized up to now ("Vaccine Handbook", pp. 103–113, Researcher's Associates, the National Institute of Health (Japan), Maruzen (Tokyo) 1996). On the other hand, there were attempts to develop an inactivated vaccine obtained without using mouse brain. More specifically, the Committee on Japanese Encephalitis Vaccine was established in 1965, and they developed a vaccine using primary cell tissue culture. However, in terms of production cost, it was practically impossible to obtain the large amount of primary cell cultures required for large-scale production of inactivated vaccine antigens. Such a vaccine was not put into practical use, because at that time, only primary culture cells were approved for production of vaccines, and the use of a passage cell line was considered to be dangerous and was not permitted. Regarding a Japanese encephalitis live vaccine obtained using tissue culture, a live vaccine using, as its active ingredient, an attenuated virus grown in primary culture of hamster renal cells in China was put into practical use in China at around 1994. However, effectiveness and safety of the live vaccine have not been confirmed, and its use in various countries other than China, is not known. Furthermore, various Japanese encephalitis vaccines obtained by recombinant gene techniques (e.g., the second generation vaccine using an envelope (E) protein antigen, recombinant virus, or the like) have been reported since about 1986. However, all of these vaccines are in the experimental stage or a pre-clinical trial stage, and they have not been put into practical use ("Vaccine", 2nd ed., pp. 671–713, S. A. Plotokin and E. A. Mortimer, W. B. Sauders Co. 1994; The Jordan Report, pp. 26–27, 1998).

Furthermore, regarding a technique of using a cell line for large-scale production of antigens or immunogens for an inactivated vaccine, for example, it is known to use a Vero cell for large-scale production of virus antigens used in vaccines against poliomyelitis (U.S. Pat. No. 4,525,349), rabies (U.S. Pat. No. 4,664,912), Hepatitis A (U.S. Pat. No. 4,783,407), and tick-borne encephalitis (U.S. Pat. No. 5,719,051), and the like. Among these, it is well-known that the former two have already been put into practical use. However, regarding the latter two, the safety and effectiveness as a vaccine of each antigen produced on a large scale have not been confirmed, and have not been put into practical use.

An active ingredient of a conventional Japanese encephalitis vaccine is inactivated particles of Japanese encephalitis virus grown in mouse brain. A large number of mice, measures against biohazard of infected animals, and the like are required for large-scale production of antigens for such a vaccine, which results in a high production cost. Furthermore, contamination into the product of adverse components derived from mouse brain (e.g., a basic protein which causes demyelination), and/or contamination of virus from a mouse, and the like, are always likely to be a factor. Therefore, purification steps and quality control become diverse and complicated. In addition, recently, it is difficult to obtain a large number of mice for production of vaccines, which becomes an obstacle to planned vaccine production. Furthermore, a conventional technique which sacrifices mice is becoming undesirable in view of animal protection and religion.

SUMMARY OF THE INVENTION

According to the present invention, virus particles are produced on a large scale by using a cell line in place of a mouse in order to solve the above problems. Because of this, the production cost can be remarkably reduced, and measures against biohazards, the operation procedure for production, purification steps, quality control, the production plan, and the like are remarkably efficient with respect to labor cost. In particular, the present invention is based on an unpredictable discovery of novel virus particles. More specifically, according to the present invention, novel virus particles, as a reinforced immunogen in which immunopotency represented as a neutralizing antibody titer is reinforced from about twice to about 10 times compared with an immunogen contained in a conventional inactivated vaccine, and a method for producing the same are provided. That is, novel Japanese encephalitis virus particles having outstanding immunogenicity or antigenicity as an inactivated vaccine against infectious disease caused by a group of Japanese encephalitis viruses, in particular as an immunogen for an inactivated Japanese encephalitis vaccine or an antigen for a diagnostic agent, and a method for producing the same are provided. Such particles are generated through the step of culturing virus belonging to a group of Japanese encephalitis viruses (e.g., Japanese encephalitis virus) in a cell line, and/or a series of subsequent steps including concentration, purification, and inactivation. However, the scientific basis for this is unknown. Based on the above, the invention described herein provides the following:

(1) an inactivated virus particle, as a reinforced immunogen, prepared from a culture of cells infected with virus belonging to a group of Japanese encephalitis viruses, wherein a neutralizing antibody titer of the anti-serum obtained by immunization with the virus particles is about twice to about 10 times the neutralizing antibody titer of the anti-serum obtained by immunization with inactivated virus particles prepared from virus cultured in mouse brain;

(2) a method for producing an inactivated virus particle, including the steps of culturing virus belonging to a group of Japanese encephalitis viruses in a cell line, as well as inactivating and purifying the cell culture;

(3) a method as described in (2), wherein the cell line is a Vero cell:

(4) a method as described in (2) or (3), wherein the inactivating is conducted before the purification;

(5) a method as described in any of (2) to (4), wherein the inactivating is conducted at a temperature in a range of about 4° C. to about 10° C.;

(6) a method as described in any of (2) to (5), wherein the purifying is conducted by physical means;

(7) a method as described in any of (2) to (6), wherein the virus belonging to a group of Japanese encephalitis viruses is a Beijing strain or a ThCMAr67/93 strain of Japanese encephalitis virus;

(8) an inactivated virus particle produced by a production method as described in any of (2) to (7);

(9) an inactivated vaccine containing inactivated virus particles as described in (1) or (8); and

(10) a diagnostic agent for infectious disease caused by a group of Japanese encephalitis viruses, containing the entirety or a part of the inactivated virus particles as described in (8) as an antigen.

BRIEF DESCRIPTION OF THE DRAWING

FIG. 1 shows electron micrographs of virus particles of the present invention (R particles; FIG. 1A) contained in a test vaccine and virus particles by conventional technologies (MB particles; FIG. 1B) contained in commercially available vaccine derived from mouse brain, with both viruses belonging to a Beijing strain.

DESCRIPTION OF THE PREFERRED EMBODIMENTS

The features of the embodiments of the present invention become apparent by comparing, in terms of both the materials and production method, an immunogen of Japanese encephalitis vaccine according to the present invention with a conventional immunogen as a representative example. Considering this, hereinafter, the difference in immunogenicity and morphology between the immunogen of the present invention and the conventional immunogen, virus particles as an immunogen, a host fore virus culture, inactivation of virus, purification of virus, electron microscopic analysis, and a potency test will be described in this order.

An immunogen of a conventional Japanese encephalitis vaccine: This refers to an active ingredient (immunogen) of a commercially available inactivated vaccine against Japanese encephalitis. It is produced under the regulations of "Japanese encephalitis vaccine" or "Freeze-dried Japanese encephalitis vaccine", an English version of which was published by the Association of Biologicals Manufacturers of Japan in 1986, stipulated by Notice No. 217 "Minimum Requirements for Biological Products" by the Japanese Ministry of Health and Welfare based on the requirements of Sec. 42(1) of the Pharmaceutical Affairs Law (Law No. 145 enacted in 1960), and which is qualified through various tests for safety, effectiveness, and the like. The active ingredient or immunogen of this vaccine is virus particles of Japanese encephalitis (i.e., inactivated virus particles derived from mouse brain (MB)). The virus particles are obtained by inoculating mouse brain with a virus strain for producing a Japanese encephalitis vaccine, allowing the virus to propagate in large quantities in mouse brain, highly purifying the virus from a mouse brain homogenate, and inactivating the virus with an inactivating agent. Hereinafter, the inactivated virus particles derived from mouse brain (MB) will be abbreviated as "MB particles" or "MB immunogen".

An immunogen of a Japanese encephalitis vaccine according to the present invention: This refers to an active ingredient (immunogen) of an inactivated Japanese encephalitis vaccine., which is produced under the above-mentioned "Japanese encephalitis vaccine" regulations except that a cell culture of a cell line is used as a host for culturing Japanese encephalitis virus, and which is qualified through various quality control tests. This immunogen is virus particles of Japanese encephalitis (i.e., inactivated virus particles derived from a tissue culture), which are obtained by inoculating a cell culture of a cell line with Japanese encephalitis virus, allowing the virus to propagate in large quantities, highly purifying the virus from the cell culture, and inactivating the virus with an inactivating agent. The immunogen has the following characteristic (1) and usually the following additional characteristic (2).

(1) A neutralizing antibody titer of the anti-serum obtained by immunization with the above particles, as measured by a potency test described below, is about twice to about 10 times the neutralizing antibody titer of the anti-serum obtained by immunization with the conventional MB particles or MB immunogen (hereinafter, the above immunogen will be referred to as "reinforced immunogen", abbreviated as "R particles or "R immunogen"); and (2) Regarding a particle structure based on electron microscopic analysis, the surface or the appearance of an envelope layer of the MB particles was smooth, whereas that of the R particles was rough or fuzzy.

It should be noted that the immunogen of a Japanese encephalitis vaccine has been described as a representative example of an immunogen of a vaccine against infectious disease caused by a group of Japanese encephalitis viruses according to the present invention. The vaccine of the present invention (e.g., Japanese encephalitis vaccine) is provided in a sealed vial or heat-sealed ampoule in a liquid or dried state. In the case of a liquid formulation, it is subcutaneously injected into a subject to be vaccinated in an amount of about 0.2 to about 1.0 ml per person. In the case of a dry formulation, it is injected after being resolubilized with a solubilizing solution.

Virus as an immunogen: The group of Japanese encephalitis viruses according to the present invention includes Japanese encephalitis virus, Kunjin virus, Murray Valley encephalitis virus, St. Louis encephalitis virus, and West Nile virus, and the like. The details thereof are as described in Archives of Virology, Supplement 10, pp. 415–427, 1995 ("Virus Taxonomy", Classification and Nomenclature of Viruses; Sixth Report of the International Committee on Taxonomy of Viruses). Among them, regarding Japanese encephalitis virus, for example, the following strains can be used: Beijing-1 strain derived from mouse brain and JWS-P-4 strain obtained by our passaging Beijing-1 strain in mouse brain (Am29 Sm1Am5; more specifically, a virus strain obtained by 29 passages in an adult mouse (Am), one passage in a suckling mouse (Sm), and 5 passages in Am), master seed JMSV001 obtained by 2 passages of JWS-P-4 in a Vero cell (hereinafter, these 3 strains will be referred to as "Beijing strain"), Nakayama-Yoken strain (hereinafter, referred to as "Nakayama strain", JaOArS982 strain, JaOH0566 strain, and ThCMAr67/93 strain and ThCMAr44/92 strain newly isolated by Igarashi et al. in the 1990s (Ali et al., Archives of Virology, 140, 1557–1575, 1995, and Ali and Igarashi, Microbiology and Immunology, 41, 241–252, 1977) and the like.

According to the present invention, among Japanese encephalitis virus strains, a Beijing strain and ThCMAr67/93 are particularly preferable as an immunogen. When these virus strains are used, a vaccine with a broad antigenic spectrum (i.e., having a very satisfactory protection against plural strains other than the virus strain used in production of the vaccine) can be obtained. Among Beijing strains, JMSV001 is preferable.

According to the present invention, a divalent vaccine may be prepared by mixing vaccines produced from two virus strains (e.g., Beijing strain and ThCMAr67/93 strain). Preferable is a mixing ratio of 0.5:1 to 1:0.5 on a basis of antigen protein contents. Because of such mixing, compared with a conventional monovalent vaccine alone, a vaccine having a broader antigenic spectrum for protecting against infection can be obtained.

A virus is cultured by inoculating an appropriate host cell line with the virus, and maintaining the infected cell in culture. A culturing method is the same as described later in "Cell culture". Hereinafter, for convenience, virus from a supernatant obtained by low-speed centrifugation of a virus culture will be referred to as "extracellular virus". Virus from a supernatant obtained by suspending infected cells collected from centrifuged pellets, in an original volume in an Eagle's Minimum Essential Medium (MEM) supplemented with 0.2% (w/v) bovine serum albumin, followed by sonication and low-speed centrifugation, will be referred to as "intracellular virus". An inactivated virus particle of the present invention can be obtained from either extracellular or intracellular virus. An extracellular virus is preferable since its yield is high; it is a mature virion; it is easy to be purified due to less contamination of cell derived components.

Host for virus culture: A known cell line can be used as a host for virus culture. For example, diploid cell lines such as WI-38, MRC-5, FRhL-2, etc., and serially passaged cell lines such as Vero, BHK-21, CHO, etc. can be used. Serially passaged cell are preferable since their large-scale production is easy and programmable, as well as they are well-characterized and confirmed not to contain any other virus. Furthermore, commonly used CV-1, BSC-1, MA104, MDCK, CaCO-2, etc., and DBS-FLC-1, DBS-FLC-2, DBS-FRhL-2, ESK-4, HEL, IMR-90, WRL68, etc. conventionally used for producing a virus vaccine can also be used ("ATCC Microbes & Cells at Work", 2nd ed., p. 144, American Type Culture Collection (ATCC) 1991, USA). For the above-mentioned host for culturing a Japanese encephalitis virus strain, preferably, permissive cells are selected which allow the virus to grow well. For example, Vero (ATCC No. CCL-81), BHK-21[C-13] (ATCC No. CCL-10), C6/36 (ATCC No. CRL-1660), etc. are preferably used. However, when using these cell lines, it is required to conduct various tests for contaminants, tumorigenicity, etc. in accordance with the Requirements for Biological Substances No. 50 regarding requirements for use of cells for the production of biologicals recommended by the World Health Organization (WHO), thereby confirming if these cell lines are qualified as cells for producing a vaccine (WHO Technical Report Series, No. 878, pp. 19–52, 1998).

Cell culture: For cell culture of the above-mentioned cell lines, stationary culture, perfusion system culture, shaking culture, roller tube culture, roller bottle culture, suspension culture, microcarrier culture, and the like can be adopted. For example, commercially available Cytodex (Pharmacia Biotech, Sweden) of various types are used as a microcarrier, and various commercially available animal cell culture devices can be used.

Inactivation of virus: An inactivating agent such as formalin, β-propiolactone, and glutardialdehyde is added to a virus suspension to inactivate the virus. For example, when using formalin, the amount to be added is about 0.005% to about 0.1% (v/v), the inactivation temperature is about 4° C. to about 38° C., and the inactivation duration mainly depends upon the inactivation temperature (e.g., about 5 to about 180 hours at 38° C., and about 20 to 90 days at 4° C.).

Purification of virus: Purification is conducted by physical means or chemical means. Physical means utilize physical properties, such as size, density, sedimentation constant, etc., of the substance to be purified, and includes, for example, zonal ultra-centrifugation, density gradient centrifugation, filtration, and the like. Physical means are usually conducted without changes in pH and salt concentration of the surrounding environment. Chemical means utilize adsorption/desorption through chemical or physico-chemical reaction and includes, for example, ion exchange column chromatography, affinity chromatography, salting, and the like. Purification is performed at about 4° C. to room temperature.

Concentration of virus: Prior to inactivation and/or purification, concentration may be performed, for example, by low-speed centrifugation with an ultrafilter membrane.

According to the present invention, inactivation of the R particles is desirably conducted at about 4° C. to about 10° C. before purification. Furthermore, purification is a desirably performed by a physical purification method. Particles thus obtained can maintain higher immunogenicity or antigenicity compared with particles inactivated after purification or chemically purified particles.

Electron microscopic analysis: For example, a virus sample prepared by a negative staining method using 2% (w/v) uranyl acetate can be observed under an electron microscope (Hitachi Ltd.). Virus particles can be analyzed on an image at a magnification of about 20,000 to about 100,000.

Preparation of vaccine: An inactivated virus particle of the present invention can be diluted with any suitable diluent so as to obtain a desired titer. Any known carrier or adjuvant may be added. A vaccine may optionally contain any preservative, stabilizer, etc.

Potency test: This test is conducted in accordance with "Potency Test" stipulated by the "Japanese encephalitis vaccine" regulations in the above-mentioned "Minimum Requirements for Biological Products". For example, fifteen 4-week old ddY mice are used in each group. The animals in each group are injected intraperitoneally with about 0.5 ml/mouse of each of the vaccines which have been serially 2-fold diluted, and after 7 days, the animals are boosted. Blood is collected from each mouse on the 7th day after the booster. Thereafter, an equal amount of serum is pooled for each group, and inactivated at about 56° C. for about 30 minutes. The resultant serum is used for a neutralizing test as an immune serum. In the neutralizing test, a chick embryo cell culture is used as a host for virus culture, and virus used as a vaccine antigen or immunogen (e.g., Beijing strain, Nakayama strain, ThCMAr67/93 strain, and the like) can be used as a challenge virus. A neutralizing antibody titer is represented by the maximum dilution at which the above-mentioned immune serum reduces the number of plaques formed by the challenge virus by about 50%.

In another aspect, the virus particle (R particles) obtained according to the present invention can be used as a diagnostic antigen (e.g., an antigen in an immunoprecipitation method, a hemagglutination inhibition (HI) test, a complement fixation (CF) reaction, an ELISA, a radioimmunoassay, an immunofluorescence method and the like). The R particles are characterized as diagnostic antigen in that reactivity of a particle with polyclonal antibodies and certain monoclonal antibodies is higher by about 2 to 10 times, compared with that of MB particles. More specifically, using the entirety or a part of an inactivated virus particle of the present invention, a diagnostic agent with high sensitivity for detecting infection by a group of Japanese encephalitis viruses, in particular infection by Japanese encephalitis virus, can be provided. As used herein, the term "a part" of an inactivated virus particle refers to a fraction of the virus which retains desired antigenicity derived from the virus particles, including, for example, structural proteins solubilized during the purification step described in Example 1.

Hereinafter, the embodiment, constitution, the structure and effect of the present invention will be described by way of illustrative experiments and examples. However, the present invention is not limited thereto.

REFERENCE EXAMPLE

The Sequence listing of both Beijing and ThCMAr67/93 strains: in order to facilitate identification of a Beijing strain and a ThCMAr67/93 strain of Japanese encephalitis virus particularly suitable for use in the present invention, SEQ ID NOs: 1 to 4 show base sequences of envelope protein gene cDNA complementary to genomic RNA of both strains and the deduced amino acid sequences encoded by the base sequences. SEQ ID NOs: 1 and 2 are for a ThCMAr67/93 strain (Archives of Virology, 140, 1557–1575, 1995), and SEQ ID NOs: 3 and 4 are for master seed virus JMSV001 which is a Beijing strain. A "Beijing strain" used in Examples below is JMSV001.

The base sequence of cDNA was determined by a method described in the above-mentioned Ali et al. article. More specifically, genomic RNA was extracted from a virus culture in Verocells. Thereafter, a region encoding for an envelope protein was amplified by reverse transcription polymerase chain reaction (RT-PCR) using a pair of primers, and the base sequence of the resultant cDNA fragment was determined by a dideoxy chain termination method. Furthermore, the amino acid sequence encoded by the base sequence was decoded using universal codes.

Experiment 1

Measurement of a virus infection titer: A virus infection titer was counted in PFUs (plaque-forming unit)/ml by a plaque-counting method using Vero-M cells described later.

Measurement of a virus antigen amount: An amount of Japanese encephalitis virus antigen was measured by ELISA using an anti-Japanese encephalitis virus monoclonal antibody IgG (Group-8 Clone 503 (kindly provided by Dr. Yasui, Tokyo Metropolitan Institute for Neurosciences; K. Yasui et al., Journal of General Virology, 67, 2663–2672, 1986). An ELISA value was calculated by a parallel line assay as a relative value when the value of an in-house standard product (Beijing strain) derived from mouse brain is defined as 100 units.

HA test: A U-shaped microplate was used. Equal amounts of 0.33% (v/v) goose red blood cell suspension adjusted to optimum pH with a phosphate buffer and virus solution were mixed. Thereafter, they were allowed to be reacted with each other at 37° C. for 60 minutes. Thus, the presence of hemagglutination was determined. An HA titer was represented as the maximum dilution of a virus solution which is positive for hemagglutination.

Measurement of an amount of a bovine serum antigen: The amount of a bovine serum antigen was measured by ELISA using anti-bovine serum goat IgG. The relative value with respect to the protein content in the bovine serum standard antigen was calculated by a parallel line assay, and the obtained value was determined as an amount of an antigen.

Experiment 2

Proliferation in a cell line for virus culture: Adhesive 2-strain Vero cells: Vero-A (ATCC No. CCL-81) and Vero-M (Vero obtained from the National Institute of Infectious Diseases); 3-strain BHK-21 cells: BHK/WI2 (adhesive BHK-21 obtained from the Osaka prefectural Institute of Public Health), BHK/JHIH (suspended BHK-21 obtained from the National Institute of Animal Health) and BHK-21 [C-13] (ATCC No. CCL-10); and a C6/36 cell (ATCC No. CRL-1660) derived from a mosquito were used as candidate cell lines for virus culture, and viral propagation in each cell line was observed. Vero-A, Vero-M, BHK/WI2, and BHK-21 [C-13] were each prepared in a growth medium at about $1.5 \times 10^5$ cells/ml. They were statically incubated at about 37° C. for 3 days, and thereafter, the number of cells were respectively counted. In the same way as this, suspended BHK/JNIH was prepared at about $2.0 \times 10^5$ cells/ml, and was incubated with shaking at about 37° C. for 3 days. Thereafter, the number of cells was counted. C6/36 was prepared at about $1.0 \times 10^5$ cells/ml, and was statically incubated at about 28° C. for 7 days. Thereafter, the number of cells was counted. As a growth medium, MEM supplemented with a 8% (v/v) (final concentration) bovine serum was used. As a result, Vero-A, Vero-M, BHK/WI2, and BHK-21 [C-13] were counted and determined to be about $7.0 \times 10^5$ cells/ml to about $9.0 \times 10^5$ cells/ml, and suspended BHK/ANIH and C6/36 were counted and determined to be about $2.8 \times 10^6$ cells/ml.

Experiment 3

Propagation of Japanese encephalitis virus in candidate cell lines: C6/36 was incubated at about 28° C. for 7 days, and the other cells used in Experiment 2 were incubated at about 37° C. for 3 days. Thereafter, each cell was inoculated with a Beijing strain at a multiplicity of infection (MOI) of 0.1, and measured for a virus infection titer (PFU), a virus antigen amount (ELISA titer), and an HA titer, whereby the time course of the change in extracellular virus amount was compared. Table 1 shows the results. Each numerical value is an average of the highest values in virus growth curves of each cell line for duplicate experiments. C6/36 exhibited the highest virus infection titer on the 3rd day from the commencement of incubation, and exhibited the highest ELISA titer and HA titer on the 4th day. The other cell lines exhibited the highest virus infection titer on the 2nd day from the commencement of incubation, and exhibited the highest ELISA titer and HA titer on the 3rd and 4th day, respectively.

TABLE 1

| Cell | PFU/ml | ELISA titer | HA titer |
| --- | --- | --- | --- |
| Adhesive | | | |
| Vero-A | $1.2 \times 10^8$ | 58 | 640 |
| Vero-M | $5.7 \times 10^7$ | 35 | 320 |
| BHK-21/WI2 | $1.5 \times 10^8$ | 27 | 40 |
| BHK-21 [C13] | $2.3 \times 10^8$ | 48 | 320 |
| Suspended | | | |
| BHK-21/JNIH | $7.0 \times 10^7$ | 37 | 40 |
| C6/36 | $2.6 \times 10^8$ | 103 | 320 |

Experiment 4

Type of Cytodex and proliferation of a Vero-A cell:
Any one of Cytodex 1, 2, or 3 was added to an amount of about 1.5 g/liter to each of 3 cell culture flasks, each containing about 500 ml of Vero-A cell suspension at about $1.5 \times 10^5$ cells/ml. Thereafter, each cell was incubated with stirring at about 37° C. and about 40 rpm for 7 days. The following results were obtained. The number of cells per milliliter on the 7th day from the commencement of incubation was about $7.5 \times 10^5$, about $8.3 \times 10^5$, and about $9.4 \times 10^5$ for Cytodex 1, 2, and 3, respectively. Furthermore, when cells were incubated with Cytodex 1 for 7 days, one hundred or more Vero-A cells were grown adhering to the surface of all the beads without any gaps.

Experiment 5

Concentration of Cytodex and proliferation of a Vero-A cell: Cytodex 1 was added to cell culture flasks A, B, C, and D, each containing about 500 ml of cell suspension at about $1.5 \times 10^5$ cells/ml, to make a final amount of about 1.5 g/liter in the flasks A and B, about 3.0 g/liter in the flask C, and about 4.5 g/liter in the flask D. Thereafter, each call was incubated with stirring at about 37° C. and about 40 rpm for 7 days. The number of cells and the fraction of beads to which cells adhered (i.e., the percentage of the beads adhered to) were counted. For calculating the percentage of the beads adhered to, at least 200 beads were observed for each flask, and the beads to which at least 5 cells adhered were counted as cell-adhered beads. The cells in the flask A in which Cytodex 1 was added to an amount of about 1.5 g/liter were incubated in the same growth medium throughout the incubation. In the flasks B, C, and D, half of the culture medium was replaced by a fresh growth medium on the 3rd, 4th, and 5th days after the commencement of incubation. The following results were obtained. Replacement of culture medium did not affect the number of cells (A and B). The number of cells per milliliter after 7-day incubation was about $9.1 \times 10^5$ for the flask B, about $7.7 \times 10^5$ for the flask C, and $8.0 \times 10^5$ for the flask D. The percentage of the beads adhered to in the flasks A and B was about 98% or higher on the 1st day, and reached 100% on the 4th day. The percentage of the beads adhered to in the flasks C and D were lower (i.e., about 93% and about 80%, respectively). However, the percentage reached 100% in the flasks A, B, C, and D on the 6th day.

Experiment 6

Proliferation of Vero-A cells incubated at a high density with Cytodex 1: High-density incubation was conducted under the condition that the concentration of Cytodex and the number of cells were tripled, respectively. Cytodex 1 was added to a Vero-A cell suspension at about $4.5 \times 10^5$ cells/ml to give a final concentration of about 4.5 g/liter, and the cells were incubated in an apparatus for incubating animal cells containing about 50 liters of a culture medium. The revolutions per minute were set to be about 15 rpm for the first 24 hours and about 20 rpm after 24 hours pH was set to be 7.0, and dissolved oxygen was set to be about 5 ppm. Half of the culture medium was replaced by a fresh growth medium on the 3rd and 5th days after the commencement of incubation. The following results were obtained. The number of cells on the 5th and 7th days was about $2.0 \times 10^6$ cells/ml and about $2.6 \times 10^6$ cells/ml, respectively. Furthermore, the percentage of the beads to which cells adhered on the 2nd day was 100%.

Experiment 7

Propagation of a virus candidate strain for producing a vaccine in Vero-A cells: Vero-A statically incubated in a petri dish for 3 days were each inoculated with the above-mentioned four candidate strains (Beijing strain, Nakayama strain, JaOH0566, and JaOArS982) of Japanese encephalitis virus derived from mouse brain at an MOI of 0.1. Virus was adsorbed to Vero-A for about 90 minutes. Then, MEM supplemented with 2% (v/v) bovine serum was added to the resultant Vero-A, followed by incubation at about 37° C. for 7 days. The time course of changes in infection titer and of an antigen amount was observed for extracellular virus and intracellular virus, were observed. The following results were obtained. Regarding the infection titer extracellular virus of the three strains other than Nakayama strain exhibited the highest value (about $1.0 \times 10^8$ PFU/ml or more) on the 2nd day after the commencement of incubation, and intracellular virus thereof exhibited a value which was ⅓ or less of that of the extracellular virus. Extracellular virus of Nakayama strain exhibited the highest infection titer on the 3rd day, which was ⅕ or less of that of the other three strains. Regarding the ELISA antigen titer, extracellular virus of the three strains other than Nakayama strain exhibited the highest value (about 70 units) on the 3rd to 5th days, and intracellular virus thereof exhibited a value which was ⅕ or less of that of the extracellular virus. The ELISA antigen titer of Nakayama strain plateaued (about 30 units) on the 5th to 7th days. Regarding the HA titer, extracellular virus of Nakayama strain exhibited a value of about 160 and that of the other three strains exhibited a value of about 640 to about 1280 on the 2nd to 4th days.

Experiment 8

Propagation of Beijing strain in a Vero-A cell incubated with Cytodex 1: 20 liters of Vero-A cells (about $1.96 \times 10^6$ cells/ml) incubated with Cytodex 1 was inoculated with Beijing strain virus 4-passaged in Vero-A at an MOI of 0.1. The cells were incubated in a bovine serum-free MEM. The following results were obtained. Intracellular virus exhibited the highest infection titer (about $1.3 \times 10^8$ PFU/ml) on the 2nd day of the incubation, and extracellular virus exhibited the highest infection titer (about $4.0 \times 10^8$ PFU/ml) on the 3rd day. Extracellular virus exhibited the highest ELISA antigen titer (about 67 units) on the 4th day, and intracellular virus exhibited the highest ELISA antigen titer (about 26 units) on the 3rd day. Extracellular virus exhibited an HA titer of about 320 and intracellular virus exhibited an HA titer of about 40 on the 3rd day of the incubation.

Experiment 9

Genetic stability of a strain: The master seed (JMSV001) was prepared by passaging mouse-derived virus (JWS-P-4) for 2 generations in Vero cells. The master seed was genetically stable even after 7 serial passages in Vero cells with no mutation found in the base sequence of a gene for each protein of Core, pre-M, and envelope. Furthermore, the amino acid sequences encoded by these genes were identical with those of JWS-P-4. Genetic analysis was conducted by the method described in Reference Example 1.

Example 1

Preparation of a test vaccine: Vero-A cells incubated using Cytodex 1 were inoculated with Beijing strain prepared by passaging mouse-derived virus (JWS-P-4) for four generations in Vero-A at an MOI of 0.1, and was incubated in a bovine serum-free MEM at about 37° C. for 4 days. A culture supernatant (i.e., extracellular virus) was collected. The supernatant was concentrated to about $\frac{1}{10}$ volume through an ultrafiltration membrane with a cutoff of 100 kDa. Thereafter, formalin was added to a final concentration of $\frac{1}{1500}$ (v/v), whereby the virus was inactivated. Inactivation was conducted at about 4° C. for 50 days. Next, an inactivated virus suspension was twice subjected to the sucrose density gradient zonal ultra-centrifugation, whereby the virus was purified. Both the first and second ultra-centrifugations were conducted at about 25% to about 50% (w/w) sucrose density gradient and about 30,000 rpm for about 13 hours, using P35ZT rotor (Nissei Sangyo Co., Ltd.). Virus fractions (sucrose density: 41%) were collected, and dialyzed against phosphate-buffered saline (PBS). The dialyzed fractions were used as a vaccine stock solution. The vaccine stock solution was subjected to various tests for safety and effectiveness in accordance with the above-mentioned "Minimum Requirements for Biological Products", and qualified as a vaccine. Then, the vaccine stock solution was diluted in TC Medium 199 (Difco Laboratories, USA) so that the protein content therein became about 7.8 µg/ml. The resultant diluted vaccine solution was dispensed in 1 ml aliquots into 3 ml vials. Thereafter, each vial was sealed to obtain a test vaccine. The protein content in the test vaccine was measured in accordance with general testing methods (wherein protein was precipitated with heated trichloroacetic acid (TCA) and quantitated by the method of the Lowry process) in the above-mentioned "Minimum Requirements for Biological Products".

Example 2

Properties of the test vaccine during main steps: Each sample which was collected at the time points of completing each of the main steps during production of the test vaccine described in Example 1 was subjected to various tests described in Experiment 1. The following results were obtained. The supernatant of virus culture (i.e., virus suspension) exhibited an infection titer of about $2.2 \times 10^8$ PFU/ml, an ELISA antigen titer of about 70 units, and an HA titer of about 160. When the virus suspension was concentrated to $\frac{1}{10}$ volume using an ultrafiltration membrane, an infection titer and an antigen amount became higher (about 10 times). After the first zonal ultra-centrifugation, peaks of virus antigen amount were observed in two fractions having a sucrose concentration of about 41% and about 34%. Electron microscopy revealed that the fraction with a sucrose concentration of about 41% contained virus particles, and the fraction with a sucrose concentration of about 34% contained virally-antigenic particles which are very much smaller than the virus particles. Furthermore, a bovine serum antigen from a cell culture was detected in the fractions having the sucrose concentration of about 28% or less, and was separated from the virus particle fractions. The above-mentioned virus particle fractions were again subjected to purification by zonal ultra-centrifugation, and the presence of virus particles were confirmed as a single peak in the fractions having a sucrose concentration of about 40%. A test vaccine was prepared from the fractions. The test vaccine exhibited an ELISA antigen titer of about 45 units, and a protein content of about 7.8 µg/ml.

Example 3

Figure 1:
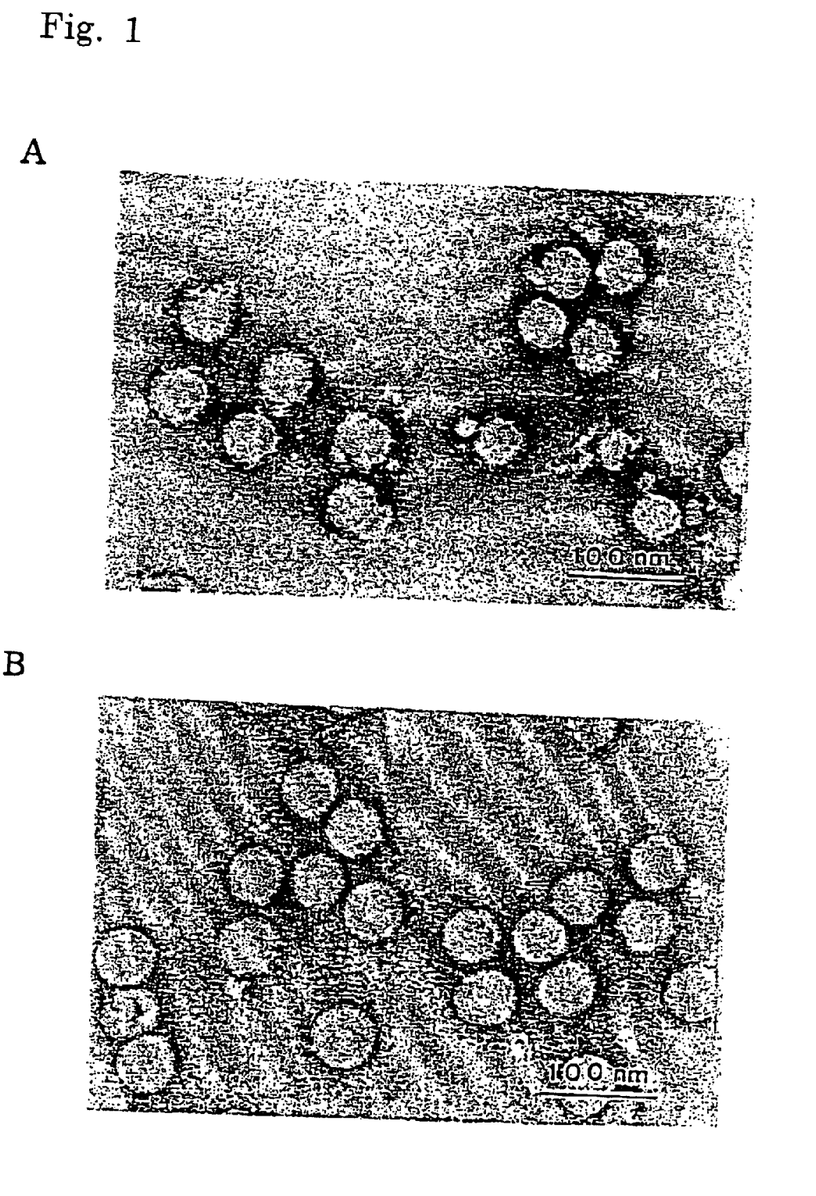

Electron microscopy of the test vaccine: The test vaccine and a commercially available vaccine derived from mouse brain were subjected to the above-mentioned electron microscopic analysis. (FIG. 1). As a result, the surface or the appearance of an envelope layer of MB particles in the commercially available vaccine was smooth (B in FIG. 1), whereas that of R particles in the test vaccine of the present invention was rough or fuzzy (A in FIG. 1).

Example 4

Potency of a test vaccine based on a neutralization reaction: Each titer of three vaccines (test vaccine obtained in Example 1, commercially available vaccine derived from mouse brain, and reference vaccine for a potency test) containing inactivated Beijing strain virus as an active ingredient was measured in accordance with the above-mentioned "potency test". More specifically, each vaccine was serially diluted 2-fold in PBS, and inoculated into mice. Neutralizing antibody titers of the serum against Beijing strain virus were compared. Table 2 shows the relationship between dilution ratios of the vaccines and common logarithm values of a neutralizing antibody titers.

The difference between common logarithmic values of neutralizing antibody titers of the anti-serum obtained by immunizing both test and commercially available vaccines (equivalent protein content) was about 0.38 to about 1.11 for vaccine dilution of 8 to 32. That is, a neutralizing antibody titer obtained by the test vaccine immunogen was about twice to about 10 times that obtained by the commercially available vaccine immunogen. Furthermore, as a result of presuming these measured values by the parallel line assay, calculated magnification of titers (neutralizing antibody titers) of the test vaccine versus the commercially available vaccine, were about 3 times.

TABLE 2

|  | Protein content µg/ml | Vaccine dilution | Common logarithmic values of Neutralizing antibody titer | Difference (A − B) |
|---|---|---|---|---|
| Test vaccine (A) | 7.8 | 8 | 3.87 | 0.64 |
|  |  | 16 | 3.51 | 0.38 |
|  |  | 32 | 3.33 | 1.11 |
| Commercially available vaccine (B) | 7.5 | 8 | 3.23 |  |
|  |  | 16 | 3.13 |  |
|  |  | 32 | 2.21 |  |
| Reference vaccine | 5.4 | 16 | 1.87 |  |

Difference (A − B): Common logarithmic value of (Neutralizing antibody titer of A) − Common logarithmic value of (Neutralizing antibody titer of B) at the identical dilution. For example, at a vaccine dilution of 8, 3.87 − 3.24 = 0.64.
Protein content: measured by a TCA protein quantitation method (a protein in a vaccine is precipitated with heated trichloroacetic acid, and is quantitated by the method of Lowry process).

Example 5

Difference in immunogenicity between test vaccines based on a cross-neutralization reaction: Three strains (Beijing strain passaged for four generations in Vero-A cells, and ThCMAr67/93 and ThCMAr44/92 derived from Thailand, passaged for two generations in Vero-A cells) were used as seed virus, and test vaccines containing inactivated virus of each strain as an active ingredient were prepared in the same way as described in Example 1. Thereafter, neutralizing antibody titers of the anti-serum obtained from mice immunized with the respective vaccines were measured and compared in the same way as described in Example 4, whereby cross-reactivity between the strains was analyzed. For comparison, commercially available vaccines derived from mouse brain containing each inactivated virus of Beijing strain and Nakayama strain as its active ingredient, and a vaccine (Beijing strain) derived from mouse brain containing 5.4 µg/ml of a TCA protein as a reference vaccine were used. Furthermore, for mouse immunization, the TCA protein content in each of five vaccines was adjusted to be about 7.5 µg/ml, and then, the vaccines were 16-fold diluted in PBS. As challenge virus in a neutralization test, the above-mentioned 4 viruses, i.e., Beijing, Nakayama, ThCMAr67/93, and ThCMAr44/92 were used. Table 3 shows the results of the above-mentioned 5 vaccines in 16-fold dilution with PBS. In view of a cross-reaction spectrum, both the virus antigens of Beijing strain and ThCMAr67/93 strain were outstanding as an immunogen of an inactivated Japanese encephalitis vaccine.

TABLE 3

| Vaccine | Virus | | | |
|---|---|---|---|---|
| | Beijing | Nakayama | Ar67 | Ar44 |
| Test vaccine (Beijing) | 3.68 | 3.04 | 2.87 | 2.66 |
| Commercially available vaccine (Beijing) | 3.09 | 2.69 | 1.88 | 1.88 |
| Commercially available vaccine (Nakayama) | 0.86 | 2.05 | 1.45 | 1.04 |
| Test vaccine (Ar67) | 2.84 | 3.15 | 3.02 | 2.97 |
| Reference vaccine (Beijing) | 1.85 | NT | NT | NT |

Ar67: ThCMAr67/93 strain; Ar44: ThCMAr44/92 strain
Test vaccine: Inactivated vaccine produced in Vero cells
Commercially available vaccine: Inactivated vaccine derived from mouse brain
Reference vaccine: In-house standard inactivated vaccine derived from mouse brain
Numerical value: Common logarithmic value (log) of neutralizing antibody titer
NT: not tried Example 6

Preparation of a test divalent vaccine: each vaccine stock solution of a Beijing strain and a ThCMAr67/93 strain was prepared in the same way as in Example 1. Thereafter, each vaccine stock solution was diluted in PBS to obtain a protein content of 10 µg/mg. Then, the resultant solutions were mixed with each other in an equal amount, and the mixture was dispensed to a vial to obtain a divalent vaccine. This divalent vaccine had a cross-reaction spectrum broader than that of the respective single monovalent vaccine.

Example 7

Preparation of a diagnostic agent: using the R particles in the Beijing strain vaccine stock solution prepared in Example 1 as a therapeutic antigen, its effectiveness was determined by ELISA in the same way as in "Measurement of a virus antigen amount" described above. As a comparative control antigen, MB particles in a In commercially available Beijing strain vaccine were used. As antibodies, the monoclonal antibody 503 (MAb503: antibody to a neutralizing epitope common and specific to all the Japanese encephalitis virus). MAb302 (antibody to an epitope specific to a group of Japanese encephalitis viruses), and a polyclonal antibody (PAb: hyper-immune serum from a mouse) were used. While the antigen amount was kept constant (7.6 µg/ml of protein amount), the antibodies were serially diluted and each ELISA value was measured. Regarding an ELISA value of the R particles/an ELISA value of the MB particles, Mab503 exhibited 53/47, Mab302 exhibited 226/22, and PAb exhibited 120/52. Based on these results, the sensitivity of the R particles to Mab302 and PAb were judged to be about twice to about 10 times higher than that of the MB particles. Furthermore, it is considered from the results of MAb302 that the antigen of the present invention is useful as antigen for preparative detection of a group of Japanese encephalitis viruses.

INDUSTRIAL APPLICABILITY

According to the present invention, virus particles are produced on a large scale by using an easy-to-handle and inexpensive cell line in place of an expensive mouse, which are also difficult to raise and control. Since a number of mice are not sacrificed, the present invention is desirable in view of animal protection. Furthermore, the production cost can be remarkably reduced, and measures against biohazards, the operation procedure for production, purification steps, quality control, the production plan, and the like are remarkably labor-efficient. According to the present invention, novel virus particles useful as a reinforced immunogen which exhibit a titer of about of twice to about 10 times that of a conventional inactivated vaccine, and a method for producing the same are provided. In particular, according to the present invention, novel Japanese encephalitis virus particles having outstanding immunogenicity or antigenicity as an immunogen for an inactivated Japanese encephalitis vaccine and an antigen for a diagnostic agent, and a method for producing the same are provided. Thus, according to the present invention, an inexpensive vaccine of outstanding quality and a diagnostic agent can be provided, which improves and dramatically spreads the prevention and diagnosis of infectious disease caused by a group of Japanese encephalitis viruses.

What is claimed is:

1. An inactivated virus particle, as a reinforced immunogen, prepared from a culture of cells infected with virus belonging to a group of Japanese encephalitis viruses, wherein the process of preparation comprises a step of inactivation followed by a step of purification solely by physical means, wherein a neutralizing antibody titer of the anti-serum obtained by immunization with the virus particles is about twice to about 10 times the neutralizing antibody titer of the anti-serum obtained by immunization with inactivated virus particles prepared from virus cultured in mouse brain wherein the particles are chemically purified and subsequently inactivated.

2. A method for producing an inactivated virus particle, comprising culturing virus belonging to a group of Japanese encephalitis viruses in a cell line, inactivating the cell culture and then purifying the virus solely by physical means, wherein a neutralizing antibody titer of the anti-serum obtained by immunization with the virus particles is about twice to about 10 times the neutralizing antibody titer of the anti-serum obtained by immunization with inactivated virus particles prepared from virus cultured in mouse brain wherein the particles are chemically purified and subsequently inactivated.

3. The method of claim 2, wherein the cell line is a Vero cell.

4. The method of claim 2, wherein the inactivating step is conducted at a temperature in a range of about 4° C. to about 10° C.

5. The method of claim 2, wherein the virus belonging to a group of Japanese encephalitis viruses is a Beijing strain or a ThCMAr67/93 strain of Japanese encephalitis virus.

6. An inactivated vaccine comprising the inactivated virus particles of claim 1.

7. A diagnostic agent for infectious disease caused by a group of Japanese encephalitis viruses, comprising the inactivated virus particles of claim 1 as an antigen.

8. The inactivated virus particle of claim 1 wherein said cells are inactivated at a temperature in a range of about 4° C. to about 10° C.

9. The inactivated virus particle of claim 1, wherein said culture of cells is a culture of Vero cells.

10. The inactivated virus particle of claim 1, wherein the virus belonging to a group of Japanese encephalitis viruses is a Beijing strain or a ThCMAr67/93 strain of Japanese encephalitis virus.

* * * * *